United States Patent [19]
Guarino et al.

[11] Patent Number: 5,162,222
[45] Date of Patent: * Nov. 10, 1992

[54] USE OF BACULOVIRUS EARLY PROMOTERS FOR EXPRESSION OF FOREIGN GENES IN STABLY TRANSFORMED INSECT CELLS OR RECOMBINANT BACULOVIRUSES

[76] Inventors: Linda A. Guarino, 404 E. 34th St., Austin, Tex. 78705; Donald L. Jarvis, 4028 Viceroy, Bryan, Tex. 77802

[*] Notice: The portion of the term of this patent subsequent to Dec. 31, 2008 has been disclaimed.

[21] Appl. No.: 583,394

[22] Filed: Sep. 17, 1990

Related U.S. Application Data

[63] Continuation-in-part of Ser. No. 377,017, Jul. 7, 1989, Pat. No. 5,077,214.

[51] Int. Cl.$^5$ .............. C12N 5/06; C12N 15/06; C12N 15/15
[52] U.S. Cl. ................... 435/240.2; 435/240.1; 435/240.21; 435/172.1; 435/320.1; 435/172.3; 536/27; 935/55; 935/60; 935/70
[58] Field of Search ........... 435/320.1, 240.2, 172.3, 435/172.1, 240.21; 536/27; 935/55, 60, 70

[56] References Cited

U.S. PATENT DOCUMENTS

| | | | |
|---|---|---|---|
| 4,745,051 | 5/1988 | Smith et al. | 435/69.51 |
| 4,879,236 | 11/1989 | Smith et al. | 435/320.1 |
| 5,017,478 | 5/1991 | Cashion et al. | 435/69.1 |

FOREIGN PATENT DOCUMENTS

| | | |
|---|---|---|
| 0260090 | 9/1987 | European Pat. Off. . |
| 0279661 | 2/1988 | European Pat. Off. . |
| WO89/07644 | 8/1989 | PCT Int'l Appl. . |

OTHER PUBLICATIONS

Blissard and Rohrmann, *Virology* 170:537–555 (1989).
Carson, et al., *Virology*, 162:444–451 (1988).
Granados and Federici (Editors), *The Biology of Baculoviruses*, vol. I, Biological Properties and Molecular Biology, Chapter 9.
Guarino and Summers, *J. Virol.* 57:563–571 (1986).
Guarino and Summers, *J. Virol.* 60(1):215–223, (1986).
Guarino, et al., *J. Virol.* 60(1):224–229 (1986).
Guarino and Summers, *J. Virol.* 61(7):2091–2099 (1987).
Summers, *Proceeding of American Society*, In Press (1990).
Webb and Summers, *Technique-A Journal of Methods in Cell and Molecular Biology*, 2(4):173–188, Aug., 1990.
IBI. Catalog. (86/87) pp. 79 & 81.

*Primary Examiner*—Robert A. Wax
*Assistant Examiner*—Christopher S. F. Low

[57] ABSTRACT

This invention details a novel and unique plasmid vector for the dual purposes of either producing transformed insect cell clones or recombinant baculoviruses. The transformed insect cell clones will continuously and permanently produce an efficiently processed desired foreign gene product. The recombinant baculoviruses will transiently express the desired foreign gene during immediate early phase of infection. This unique vector employs promoters from two different immediate early baculovirus genes along with the natural occurring polyhedrin promoter and gene. This unique combination creates a situation where the virus is highly infectious in vivo and resistant to inactivation in nature, because it is occlusion positive, and expresses the foreign gene product during immediate early phase of infection. Therefore this virus would be very effective as a delivery system of pesticides.

20 Claims, 3 Drawing Sheets

FIG.1

1. pIE1Neo
VECTOR  IE1 PROMO  G418-RESISTANCE CODING  3'IE1 SEQUENCES  VECTOR 2. p39E⁻Neo
VECTOR  39K PROMO  G418-RESISTANCE CODING  3'39K SEQUENCES  VECTOR 3. p39E⁺Neo
VECTOR  hr 5  39K PROMO  G418-RESISTANCE CODING  3'39K SEQUENCES  VECTOR 4. pIE139Neo
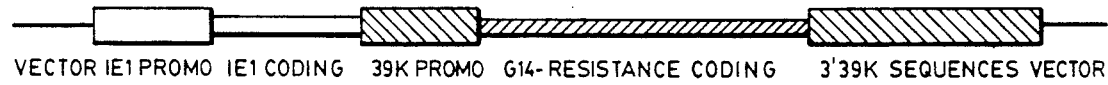
VECTOR IE1 PROMO  IE1 CODING  39K PROMO  G14-RESISTANCE CODING  3'39K SEQUENCES VECTOR 5. p510 Neo
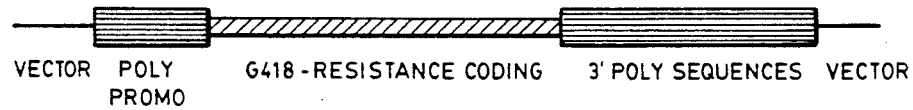
VECTOR  POLY PROMO  G418-RESISTANCE CODING  3' POLY SEQUENCES  VECTOR 6. pIE1NFB
VECTOR IE1 PROMO  IE1+β-GALACTOSIDASE CODING  3'IE1 SEQUENCES  VECTOR 7. pIE1NFB
VECTOR IE1 PROMO  β-GALACTOSIDE CODING  3'IE1 SEQUENCES  VECTOR 8. p39E⁺FB
VECTOR  hr5  39K PROMO  β-GALACTOSIDASE CODING  3'39K SEQUENCES  VECTOR 9. pIE1tPA
VECTOR IE1 PROMO  tPA CODING  3'IE1 SEQUENCES  VECTOR

USE OF BACULOVIRUS EARLY PROMOTERS FOR EXPRESSION OF FOREIGN GENES IN STABLY TRANSFORMED INSECT CELLS OR RECOMBINANT BACULOVIRUSES

The Government may have rights in this invention pursuant to a funding agreement with the National Science Foundation (NSF), Grant No. DMB-88 04732.

This application is a continuation in part of copending U.S. Ser. No. 07/377,017, filed Jul. 7, 1989 now U.S. Pat. No. 5,077,214.

BACKGROUND OF THE INVENTION

A. Field of the Invention

This invention relates to recombinant DNA vectors useful for producing recombinant baculovirus or stably-transformed insect cell lines.

B. Description of the Related Art

Baculovirus expression vectors (BEVs) have become extremely important tools for the expression of foreign genes, both for basic research and for the production of proteins with direct clinical applications in human and veterinary medicine (W. Doerfler, *Curr. Top. Microbiol. Immunol.*, 131:51–68 (1968); V. A. Luckow and M. D. Summers, *Bio/Technology*, 6:47–55 (1988a); L. K. Miller, *Annual Review of Microbiol.*, 42:177–199 (1988); M. D. Summers, *Curr. Communications in Molecular Biology*, Cold Spring Harbor Press, Cold Spring Harbor, N.Y. (1988)). BEVs are baculovirus recombinant insect vectors in which the coding sequence for a chosen foreign gene has been inserted behind the promoter in place of the nonessential viral gene, polyhedrin (Smith and Summers, U.S. Pat. No., 4,745,051).

Baculovirus genes are expressed in a sequential, temporally-regulated fashion during one or more of four different phases of the viral replication cycle (P. D. Friesen and L. K. Miller, *Curr. Top. Microbiol. Immunol.*, 131:31–49 (1986); L. A. Guarino, CRC Press, (1989) [in press]). Therefore, different baculovirus genes may be classified as immediate-early ($\alpha$), delayed-early ($\beta$), late ($\gamma$), or very late ($\delta$), according to the phase of the viral infection during which they are expressed.

The expression of these genes occurs sequentially, probably as the result of a "cascade" mechanism of transcriptional regulation. Thus, the immediate-early genes are expressed immediately after infection, in the absence of other viral functions, and one or more of the resulting gene products induces transcription of the delayed-early genes. Some delayed-early gene products, in turn, induce transcription of late genes, and finally, the very late genes are expressed under the control of previously expressed gene products from one or more of the earlier classes. One relatively well-defined component of this regulatory cascade is IE1, an immediate-early gene of *Autographa californica* nuclear polyhedrosis virus (AcMNPV). IE1 is expressed in the absence of other viral functions and encodes a product that stimulates the transcription of several genes of the delayed-early class, including the 39K gene (L. A. Guarino and M. D. Summers, *J. Virol.*, 57:563–571 (1986a); *J. Virol.*, 61:209–2099 (1987)), as well as late genes (L. A. Guarino and M. D. Summers, *Virol.*, 162:444–451 (1988)). However it is believed that the immediate-early genes are not dependent upon other viral genes for expression.

The polyhedrin gene is classified as a very late gene. Therefore, transcription from the polyhedrin promoter requires the previous expression of an unknown, but probably large number of other viral and cellular gene products. Because of this, state-of-the-art BEVs, such as the exemplary BEV system described by Smith and Summers (U.S. Pat. No., 4,745,051) will express foreign genes only as a result of gene expression from the rest of the viral genome, and only after the viral infection is well underway. In addition, this vector is not suitable for expression in live insects because it cannot produce occluded viral progeny.

The expression of foreign genes as a result of gene expression from the rest of the viral genome represents a clear limitation to the use of the traditional BEV system for at least two reasons. First, infection with the essentially intact recombinant virus ultimately kills the host cell, thereby terminating its role as a "factory" for foreign protein production. Therefore, disadvantages to the expression of foreign genes under the control of baculovirus "very late" promoters (polyhedrin and p10 genes) are that expression from these promoters can only occur in insect cells infected with a recombinant baculovirus during the very late phase of the infection. Because these host cells die after 4–5 days of infection, expression with these vectors is what is defined as transient. Thus, prior art BEV systems are limited to transient gene expression in cell lines.

The second limitation is the decrease in the ability of the host cell to process newly synthesized proteins as the baculovirus infection progresses (D. L. Jarvis and M. D. Summers, *Mol. Cell. Biol.*, 9:214–223 (1989)). After only one day of infection, the infected cells no longer process foreign glycoproteins efficiently, as previously shown for human tissue plasminogen activator. Thus, gene expression from the polyhedrin promoter occurs at a time when the host cell's ability to process newly synthesized proteins is significantly diminished.

Thus, there is a great need for a system that expresses foreign gene products in a continuous and permanent manner such that the cell is still capable of processing glycoprotein products efficiently. Described herein is such a system, as well as an improved and novel vector for gene expression employing baculovirus early promoters.

The novel and improved plasmid vector described in this invention can be used to produce either insect cell transformants or recombinant baculoviruses. This vector expresses a foreign gene either in uninfected insect cells or during the immediate early phase of infection in insect cells or in insects found in nature. Thus, this plasmid vector is suitable for expression in live insects because it can be incorporated into recombinant viruses that can produce occluded viral progeny. This novel plasmid vector retains a functional polyhedrin gene which is necessary to stabilize the virus against environmental inactivation.

This also allows the recombinant viruses produced with these plasmid vectors to produce occluded progeny. These progeny are highly infectious in vivo. This is not true for other recombinant baculoviruses, which produce only non-occluded progeny. Thus, the new vectors will have the ability to express foreign genes in vivo and expression will occur during the early stages of infection. These properties are particularly critical for the expression of foreign gene products, including insecticides, in insects. Together, these features make this vector ideal for use in environmental applications particularly for pest control.

This invention has direct utility in terms of effectively disseminating potent insecticides to the environment. One of the novel aspects of this invention is the use of early baculovirus gene expression for effective insecticide delivery. Insect viral infections, because of a late baculovirus promoter, normally take 3–5 days to kill the insect. During this time the insects will continue to feed on the crop. In 3–5 short days, insects infected with viruses can devastate the crops and the farmer's future. Thus, by using insecticides under the direct control of promoters derived from early baculovirus genes, insects will be killed or at least prevented from continuing to feed on the crops. Death of the insect or prevention from further feeding should occur within hours of ingesting viruses.

Another advantage for baculovirus expression vector system users is infected cells are healthier while still producing the desired foreign genes.

SUMMARY OF THE INVENTION

In general and overall scope, this invention describes a vector capable of producing either transformed non-infectious insect cell clones that continuously and permanently expresses a desired foreign gene or a recombinant baculovirus that transiently expresses the desired foreign TM gene. These alternative products are independently generated depending on the particular method used with this unique vector. This novel and unique vector can therefore be used to produce either (1) insect cell transformants (uninfected) expressing the desired gene constitutively and continuously or (2) recombinant baculoviruses (infected) expressing the desired gene during the immediate early phase of infection in insect cells or in insects themselves.

The insertion of the desired gene in the uninfected insect cell transformants produce stably transformed cell clones where the DNA coding for the desired gene is stably integrated into the insect host cell's genome. This stable integration of foreign DNA into host cell's genome allows for continuous and permanent expression of that desired gene. The continuously expressed product can then be purified from a portion of the population of cells. The stably transformed insect cell therefore becomes a factory that continuously expresses a desired gene. "Stably transformed insect cells," "stable integration into the host insect cell's genome" and "transformed insect cells" all describe the same or an essentially similar event of stable integration of foreign DNA into the host cell genome and the subsequent expression of this desired gene on a continuous and permanent basis.

Optimally, the most preferred embodiments for the novel plasmid vector that produces a transformed insect cell clone (uninfected) continuously and permanently expressing the desired gene, contains the following components directionally positioned from left to right:

1. a DNA region encoding for a selectable marker gene (for example, DNA encoding for the β-galactosidase gene). This selectable marker gene is positioned upstream and in frame to the DNA region encoding a first promoter region of element 2;
2. a DNA region comprising a first promoter region derived from a baculovirus immediate-early gene (for example, IEN) directionally positioned to drive the expression of the marker gene upstream of this promoter;
3. a DNA comprising a second promoter region derived from another baculovirus immediate-early gene (for example, IE1) and directionally positioned and appropriately spaced to drive the expression of the desired gene;
4. a DNA region comprising a cloning restriction site available for insertion of a cDNA or genomic DNA sequence encoding a desired protein. This cloning restriction site comprises a multiple cloning cassette sequence positioned downstream and in frame to the first nucleotide of the second promoter region of element B;
5. a cDNA or genomic region encoding a desired gene positioned at the cloning restriction site and in frame with the second promoter, whereby the second promoter region drives the expression of the desired gene.

Thus, this invention further encompasses a transformed insect cell clone comprising the baculovirus transfer vector described above.

Optimally, the most preferred embodiments for the novel plasmid vector that produces recombinant baculoviruses (infected) expressing the desired gene during the immediate early phase of infection in insect cells or in insects themselves, contains the following components directionally positioned from left to right:

1. a baculovirus viral DNA sequence encoding a portion of the 5' end of flanking polyhedrin gene (this flanking sequences is essential for efficient homologous recombination of pIETV into the polyhedrin gene of baculovirus);
2. a DNA region encoding for a selectable marker gene (for example, DNA encoding for the β-galactosidase gene). This selectable marker gene is positioned upstream and in frame to the DNA region encoding a first promoter region of element 3;
3. a DNA region comprising a first promoter region derived from a baculovirus immediate-early gene (for example, IEN) directionally positioned to drive the expression of the marker gene upstream of this promoter;
4. a DNA region comprising a second promoter region derived from another baculovirus immediate-early gene (for example, IE1) and directionally positioned and appropriately spaced to drive the expression of the desired gene;
5. a DNA region comprising a cloning restriction site available for insertion of a cDNA or genomic DNA sequence encoding a desired protein. This cloning restriction site comprises a multiple cloning cassette sequence positioned upstream and in frame to the DNA region encoding the polyhedrin gene of element 6, and positioned downstream to the first nucleotide of the second promoter region of element B;
6. a cDNA or genomic region encoding a desired gene positioned at the cloning restriction site and in frame with the second promoter, whereby the second promoter region drives the expression of the desired gene.
7. a DNA region encoding polyhedrin gene including the polyhedrin promoter;
8. a baculovirus viral DNA sequence encoding a portion of the 3' end of flankink polyhedrin gene (this flanking sequences is essential for efficient homologous recombination of pIETV into the polyhedrin gene of the baculovirus).

Thus, this invention further encompasses a recombinant baculovirus comprising the baculovirus transfer vector described above.

Yet another preferred embodiment of this invention is a method for specifically generating the desired end product from the plasmid vectors described above (either stably in a transformed insect cell clone or transiently in a recombinant baculovirus).

These plasmid vectors contain a marker gene for the quick and easy identification of the desired transformed cell clones or recombinant viruses. The marker gene could be one of many different available marker genes known to those skilled in the art, however in the most preferred embodiment, the marker gene is β-galactosidase, chloramphenicol acetyltransferase or beta-glucuronidase. Thus, desired transformed cell clones or recombinant viruses can be detected by the production of the marker gene (i.e. β-galactosidase).

Another preferred embodiment of this plasmid vector is the use of two baculovirus early promoters for gene expression in host insect cells. Any of the early baculovirus promoters would be efficient in this system, however, IEN, IE0, and IE1 are preferred for this invention. The inventors prefer to employ the early promoter region derived from the immediate-early IEN gene to drive the expression of the marker gene, for example, β-galactosidase which is used to facilitate the identification of insect cell transformants or recombinant viruses. IEN drives the expression of a marker gene in one directional orientation and the other early promoter region, most preferably derived from the immediate-early gene IE1, is oriented in the other direction. Since the two baculovirus promoters are positioned in opposite directions, there is no need for the two early baculovirus promoters to be different.

In the most preferred embodiment, the IE1 promoter region is followed by a multiple cloning cassette which functions to facilitate the insertion, in the proper orientation, of a desired foreign gene. This multiple cloning cassette sequence is positioned downstream to the IE1 promoter. A typical cassette sequence cartridge would include restriction sites for 8-11 different enzymes (for example, HincII, EcoRI, XhoI, SmaI, PstI, SacII, NheI, NcoI, NotI, BstBI). Multiple cloning cassette sequence cartridges are commercially available from several different companies (Promega, New England Biolabs, etc.) or can be synthesized in individual laboratories using a DNA synthesizer. Either method is routinely employed and the availability of these cassette cartridges are known to those skilled in the art.

In another embodiment of the invention, an immediate-early gene as described above is used in combination with a baculovirus gene promoter region of the delayed-early category. Unlike the immediate-early genes, such delayed-early genes require the presence of other viral genes or gene products such as those of the immediate-early genes. The combination of immediate-early genes can be made with any of several delayed-early gene promoter regions such as 39K or one of the delayed-early gene promoters found on the HindIII-k fragment of the baculovirus genome. In a preferred embodiment, the 39K promoter region is linked to the heterologous gene of interest and expression is further controlled by the presence of IE1.

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences (hr1, hr2, hr3, hr4 and hr5) are characterized by their enhancement of delayed-early gene expression in situations where the immediate-early gene or its product is limited. In a preferred embodiment, the hr5 enhancer sequence is linked directly (in cis) to the delayed-early gene promoter region, 39K, thereby enhancing the expression of the cloned heterologous DNA.

In addition to the above components, the unique plasmid vector includes a DNA region comprising a cDNA or genomic DNA sequence coding for a desired protein derived from a eukaryotic or prokaryotic source. Sequences coding for a variety of different genes are known to those skilled in the art and are commercially available from American Type Culture Collection (ATCC, Rockville, Maryland). For example, the following is a brief list representing the range of cloned genes or probes available from ATCC: epidermal growth factor receptor, β-glucuronidase, Y-mos M1 Maloney sarcoma virus, tissue-type plasminogen activator, arginosuccinate synthetase, insulin (A and B chain), prolactin, interleukin 1 and 2, colony stimulating factor, tumor necrosis factor, β-hemoglobulin, interferon, leutinizing hormone, β-hexosaminidase, coagulation factor VIIIC, transferrin, esterase D, adenosine deaminase, etc.

Yet another embodiment for this plasmid vector is the intact polyhedrin gene and promoter which allows for the production of occluded progeny by the recombinant viruses. Since the recombinant viruses produced with these plasmid vectors are capable of synthesizing polyhedrin, they will produce occluded progeny. These recombinant viruses are highly infectious in vivo and also resist environmental inactivation. This capability, which does not exist in other recombinant baculoviruses, allows infection and foreign gene expression in insects during the early stages of infection. In insects, these properties are particularly essential for the expression of foreign gene products, including insecticides. Together, these features make this vector ideal for use in environmental applications, particularly for pest control.

This cDNA sequence is further comprised of nucleotide sequences coding for a desired protein having a deleted 5' untranslated region, and its own translational initiation site. In terms of this invention, amino acid and nucleotide numbers will be used interchangeably with the appropriate conversion factor employed.

Appropriate positional spacing between the numerous recombinant DNA vector components (directionally positioned 5' to 3') is determined for each specific DNA coding for a desired protein and this information is included to further optimize the expression and production of the desired protein.

In one embodiment, the early gene promoter region is derived from a baculovirus. The baculovirus can be any one of a number of viruses of insect cells including *Autographa californica* MNPV, *Trichoplusia ni* MNPV, *Rachiplusia ou* MNPV *Orgyia psuedosugata* NPV, *Bombyx mori* NPV, *Heliothis zea* NPV, *Spodoptera exigua* NPV or *Galleria mellonella* NPV.

In a most preferred embodiment, the early gene promoter region is derived from the baculoviral DNA of *Autographa californica* MNPV, where said early gene promoter region is capable of being expressed in the cells of *Spodoptera frugiperda*. The early gene promoter region isolated from baculovirus may be an immediate-early gene of the virus such that no additional viral gene or gene product is needed in order to get constitutive expression of the heterologous gene. The immediate-early gene from which the promoter region is derived may be either IE1 or IEN. In a preferred embodiment, the gene promoter region is isolated from the immediate-early gene of baculovirus, IE1.

Once the method of this invention is utilized as described above, it is possible to derive stably-transformed insect cell clones of interest. These transformed insect cell clones will therefore comprise the baculovirus transfer vector described above. In the most preferred embodiment of this invention, the transformed insect cell clone will be a Lepidopteran transformed insect cell clone. The transformed cell clones may be derived from any of the available Lepidopteran insect cell lines including from *Spodoptera frugiperda, Bombyx mori, Heliothis virescens, Heliothis zea, Mamestra brassicas, Estigmene acrea* or *Trichoplusia ni.*

In the most preferred embodiment, a stably-transformed Sf9 cell line of *Spodoptera frugiperda* is constructed which expresses a heterologous DNA of interest under the control of any early gene promoter or combination of early gene promoters for over 100 passages of growth. In its most preferred embodiment, the Sf9 cells utilized will be those cells which are in the log phase of growth. The heterologous DNA product of such a stably-transformed cell line is, in the most preferred embodiment, post-translationally modified and-/or secreted by the cell line since the cellular machinery of these cells is substantially unchanged by the presence of the early gene sequences of the virus.

BRIEF DESCRIPTION OF THE DRAWINGS

FIG. 1 schematically shows the construction of the recombinant plasmids pIE1Neo, p39E⁻Neo, p39E⁺Neo, pIE139Neo, p510Neo, pIE1FB, pIE1NFB, p39FB and pIE1tPA.

DETAILED DESCRIPTION OF THE PREFERRED EMBODIMENTS

Figure 2:
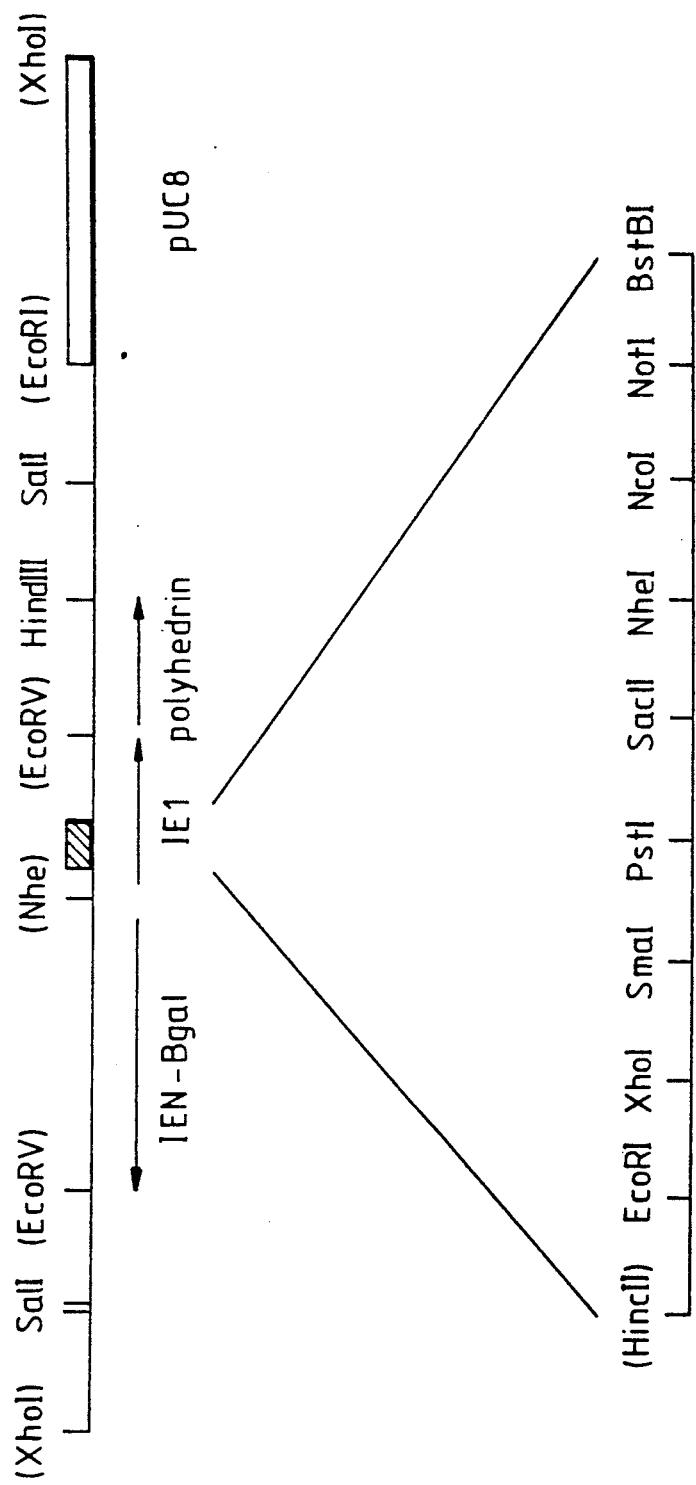
FIG. 2 diagrams the immediate early transfer vector (pIETV). pIETV is constructed from the EcoRI fragment of AcNPV DNA. Parenthesis indicate sites destroyed during construction. Arrows indicate direction of transcription of the indicated genes; arrow heads indicate poly-adenylation sites. Shaded box indicates a multiple cloning site sequence (sequence shown in lower portion of the figure).

As used herein, the term baculovirus early gene includes baculovirus immediate-early genes and baculovirus delayed-early genes. Immediate-early genes are comprised of any viral gene which is expressed in uninfected cells, and includes the genes IE1 and IEN. Delayed-early genes are any viral genes which are activated in trans by an immediate-early gene product, such as IE1 or IEN. The AcMNPV 39K gene is an exemplary delayed-early gene, as are the four delayed-early transcripts of the HindIII-k fragment of AcMNPV.

Transcription from delayed-early genes under the control of immediate-early gene products can be enhanced in the presence of a cis-linked enhancer such as hr1, hr2, hr3, hr4 or hr5.

As used herein, the term heterologous gene or heterologous DNA comprises those exogenous sources of DNA which include eukaryotic genes or DNA, prokaryotic genes or DNA and further includes genes or DNA of viral origin.

The examples herein are illustrative of laboratory techniques found by the present inventors to constitute preferred modes for practicing various aspects of the invention. However, those of skill in the art, in light of the present disclosure, will appreciate that various modifications and alterations can be made in the structuring and carrying out of the invention, and still remain within the spirit and scope of the invention.

Deposit of Plasmids

The preferred plasmid, pIE1 containing the immediate-early baculovirus promoter IE1, was deposited with American Type Culture Collection, (Rockville, Maryland) on Jul. 6, 1989 and is assigned accession number 40630. The preferred plasmid, p39E+ containing the delayed-early promoter 39K and the transcriptional enhancer element hr5, was deposited with American Type Culture Collection (Rockville, Maryland) on Jul. 6, 1989, and is assigned accession number 40629. The preferred plasmid, pHindIIIK containing the four delayed-early transcripts of the HindIII-k fragment of AcMNPV, was deposited with American Type Culture Collection, (Rockville, Maryland) on Jul. 6, 1989 and is assigned accession number 40628.

Experimental

STARTING MATERIALS AND METHODS

According to the preferred embodiment of this invention, the neomycin resistance gene (Neo-R), is utilized and was obtained according to the methods set forth in P. J. Southern and P. Berg, *J. Mol. Appl. Gen.*, 1:327-341 (1982). However, those skilled in the art who have the benefit of this disclosure will recognize that other antibiotic resistance genes may be suitably utilized. In particular, it is expected that at least the hygromycin B resistance gene (Hygro-R) and the methotrexate resistance gene (Metho-R) obtained according to the methods set forth in J. C. Li and E. Kaminskas, PNAS, 81:5694-5698 (1981) and may be utilized to advantage.

Viral DNA

The baculovirus *Autographa californica* nuclear polyhidrosis virus (AcMNPV), used in the examples as the original source of viral DNA was isolated according to procedures described in G. E. Smith and M. D. Summers, *Virology*, 89:517-520 (1978) and G. E. Smith and M. D. Summers, J Virol., 39:125-137 (1981).

According to the preferred embodiment of this invention, a particular strain of AcMNPV, E2, may be utilized. However, those skilled in the art who have the benefit of this disclosure will recognize that other baculoviruses and other baculovirus strains ma also be suitably utilized to obtain viral DNA. In particular, it is expected that at least the closely related and naturally occurring strains *Trichoplusia ni* MNPV, *Rachiplusia ou* MNPV, *Galleria mellonella* MNPV and any plaque-purified strains such as the M3, R9, S1 and S3 strains of AcMNPV isolated and characterized in G. E. Smith and M. D. Summers, *J. Virol.*, 33:311-319 (1980) may be utilized to advantage. Further description of those and other strains are found in G. E. Smith and M. D. Summers, Virol., 89:517-527 (1978).

Enzymes

Restriction enzymes and other enzymes used in these constructions were obtained either from Bethesda Research Laboratories (Bethesda, Maryland), Promega (Madison, Wisconsin), or New England Biolabs, Inc. (Beverly, Massachusetts).

β-gal DNA

The DNA fragment comprising the β-galactosidase gene used in the examples was isolated from the plasmid pDP500, obtained from Dr. Max D. Summers, Dept. of Entomology, Texas A&M University, College Station, Texas 77843. (See V. A. Luckow and M D. Summers, *Virol.,* 167:56–71 (1988b)). Plasmids containing the DNA fragment comprising the β-galactosidase gene are available from American Type Culture Collection (Rockville, Maryland).

tPA DNA

The DNA fragment comprising the human tissue plasminogen activator gene used in the examples was isolated from the plasmid pVL327, obtained from Dr. Max D. Summers, Dept. of Entomology, Texas A&M University, College Station, Texas 77843. (See V. A. Luckow and M. D. Summers, *Virol.,* 167:56–71 (1988b)). Plasmids containing the DNA fragment comprising the human tissue plasminogen activator gene are available from American Type Culture Collection (Rockville, Maryland).

Insect Cell Lines

The Lepidopteran insect cell line IPLB-Sf21-AE was established more than ten years ago from the fall armyworm, *Spodoptera frugiperda* (J. L. Vaughn, *et al., In Vitro,* 13:213–217 (1977)).

The *Spodoptera frugiperda* Sf9 cell line was obtained from American Type Culture Collection (Rockville, Maryland) and is assigned accession number ATCC CRL 1711. See M. D. Summers and G. E. Smith, *A Manual of Methods for Baculovirus Vectors and Insect Cell Culture Procedures,* Texas Agricultural Experiment Station Bulletin No. 1555, Texas A&M University (1987). Those skilled in the art who have the benefit of this disclosure will recognize that other clonal derivatives of the Sf9 cell line can be utilized to advantage.

Cell Medium

The TNMFH medium used in the examples was prepared according to the methods of M. D. Summers and G. E. Smith, *A Manual of Methods for Baculovirus Vectors and Insect Cell Culture Procedures,* Texas Agricultural Experiment Station Bulletin No. 1555, Texas A&M University (1987). (See also W. F. Hink, *Nature (London),* 226:466–467 (1970)). The fetal calf serum used to supplement the TNMFH medium can be obtained from Hazelton Research Products, Inc. (Lenexa, Kansas).

Antibiotics

The neomycin antibiotic, G418 used in the examples was obtained from GIBCO, (Grand Island, New York). Hygromycin B and methotrexate antibiotics are also commercially available from Sigma Chemical Company, (St. Louis, Missouri).

Methods

All plasmids were constructed and purified using standard recombinant DNA techniques described in T. Maniatis, E. F. Fritsch and J. Sambrook, *Molecular Cloning: A Laboratory Manual,* Cold Spring Harbor Laboratory (1982) under the current regulations described in United States Dept. of HEW, *National Institute of Health (NIH) Guidelines for Recombinant DNA Research.* These references include procedures for the following standard methods: cloning procedures with E. coli plasmids, transformation of *E. coli* cells, plasmid DNA purification, phenol extraction of DNA, ethanol precipitation of DNA, agarose gel electrophoresis, purification of DNA fragments from agarose gels, and restriction endonuclease and other DNA-modifying enzyme reactions.

The standard methods of insect cell culture, cotransfection and preparation of certain plasmids, including pAc510 and pAc360-β-gal, used in accordance with the examples, are set forth in M. D. Summers and G. E. Smith, *A Manual of Methods for Baculovirus Vectors and Insect Cell Culture Procedures,* Texas Agricultural Experiment Station Bulletin No. 1555, Texas A&M University (1987). This reference also pertains to the standard methods of cloning genes into AcMNPV transfer vectors, plasmid DNA isolation, transferring genes into the AcMNPV genome, viral DNA purification, radiolabelling recombinant proteins and preparation of insect cell culture media.

The procedures for the cultivation of viruses and cells are described in L. E. Volkman and M. D. Summers, *J. Virol,* 19:820–832 (1975) and L. E. Volkman, M. D. Summers and C. H. Hsieh, *J. Virol,* 19:820–832 (1976). Viral growth kinetics were determined as described by L. E. Volkman, et al., supra, using *S. frugiperda* and a 1.5% agarose overlay.

Biochemical analyses

Total cellular DNA was extracted from Sf9 cells (passage 26, hereafter "P26") or clonal derivatives (IE1FB1, P21; IE1FB2, P21; IE1FB4, P20; IE1FB5, P20; and IE1FB7, P19) by standard methods described in T. Maniatis, E. F. Fritsch and J. Sambrook, *Molecular Cloning: Laboratory Manual,* Cold Spring Harbor Laboratory (1982). Hirt lysates were prepared from Sf9 cells or clonal derivatives (IE1FB1, P17; IE1FB2, P16 and 49; IE1FB4, P21; and IE1FB7, P15 as described previously in B. Hirt, *J. Mol. Biol.,* 26:365–369 (1967). DNA samples were analyzed for the presence of plasmid sequences by the method of E. M. Southern, *J. Mol. Biol.,* 98:503–517 (1975). The probes used for Southern analyses were labelled with [$\alpha$-$^{32}$P]dATP (New England Nuclear, Boston, Massachusetts; 800 Ci/mmol) by the random primer method of A. P. Feinberg and B. Vogelstein, *Analyt. Biochem.,* 132:6–13 (1983). Southern blots were hybridized and washed under high stringency conditions as described previously in J. G. W. Fleming and M. D. Summers, *J. Virol.,* 57:552–562 (1986). Total cellular RNA was extracted by the method of J. M. Chirgwin et al., *Biochemistry,* 18:5294–5299 (1979), and was subjected to S1 nuclease protection analysis according to the methods in R. F. Weaver and C. Weissman, *Nucleic Acids Res.,* 7:1175–1193 (1979). Probes for S1 mapping were gel-purified restriction fragments 5′ end-labeled with polynucleotide kinase. Total cellular proteins were detergent-extracted and analyzed either by the radioimmunoprecipitation methods in S. W. Kessler, *J. Immunol.*, 115:1617–1624 (1975) and the sodium dodecyl sulfate polyacrylamide gel electrophoresis (SDS-PAGE) methods in U. K. Laemmli, *Nature*, 227:680–685 (1970), or by the SDS-PAGE and western blotting methods of H. Towbin, T. Staehlin and J. Gordon, *Proc. Natl. Acad. Sci. U.S.A.*, 76:4350–4354 (1979), as described previously in D. L. Jarvis and M. D. Summers, *Mol. Cell. Biol.*, 9:214–223 (1989). Immune complexes were detected in western blots by the alkaline phosphatase method set forth in M. S. Blake, et al., *Anal. Biochem.*, 36:175–179 (1984). Assays for β-galactosidase activity were performed using a modification of the method of I. Zamn and A. Fowler, in: *The Lactose Operon*, p. 27, Cold Spring Harbor Press, Cold Spring Harbor, New York (1970). Units of β-galactosidase activity are expressed in Tables 1 and 2 as the change in absorbance at 420 nm per hour per million cells. One unit of activity equals an increase of 1.0 absorbance units after incubation of the extract from $1 \times 10^6$ cells per one hour.

Immunofluorescence

Indirect immunofluorescence was used to visualize antigens in Sf9 cells or their clonal variants. The cells were grown on coverslips for various time periods, rinsed with PHEM buffer (60mM PIPES, 25 mM HEPES, 10 mM EGTA, 2 mM $MgCl_2$, pH 6.9; REF) and fixed in formaldehyde (2% w/v in PHEM; freshly prepared from paraformaldehyde) for 20 minutes at room temperature. The cells were rinsed with PHEM, treated with 0.1% Triton-X-100 in PHEM for another 20 minutes at room temperature, and rinsed with Dulbecco's phosphate-buffered saline (DPBS). The fixed and solubilized cells then were incubated for 30 minutes in a humidified chamber at room temperature with primary antibody (e.g., mouse-anti-β-galactosidase; Promega; Madison, Wisconsin) diluted in DPBS containing 2% normal goat serum. The cells were rinsed with DPBS, then incubated with secondary antibody (e.g. goat-anti-mouse-IgG-FITC; Organon Teknika Corporation; West Chester, Pennsylvania) under the conditions described above. Finally, the cells were rinsed with DPBS and water, and mounted for fluorescence microscopy and photography using an Olympus Vanox Model AHBT microscope (Olympus Optical Co., LTD.; Tokyo, Japan.)

EXAMPLE I

Construction of Recombinant Plasmids

All constructs used in the examples are shown schematically in FIG. 1. The plasmid pIE1Neo contains the neomycin resistance gene, Neo-R (P. J. Southern and P. Berg, *J. Mol. Appl. Gen.*, 1:327–341 (1982)), immediately downstream of the IE1 promoter (L. A. Guarino and M. D. Summers, *J. Virol.*, 57:563–571 (1986a); *J. Virol.*, 61:2091–2099 (1987). This plasmid was constructed by inserting a repaired BolII-BamHI fragment encoding Neo-R into a HincII site 39 base pairs upstream of the translational start site for IE1.

The plasmid p39E+Neo contains the promoter for 39K (L. A. Guarino and M. D. Summers, *J. Virol.*, 57:563–571 (1986a)), with the AcMNPV transcriptional enhancer element, hr5, (L. A. Guarino and M. D. Summers, *J. Virol.*, 60:215–223 (1986b); L. A. Guarino et al., *J. Virol.*, 60:24–229 (1986)), located upstream, and the Neo-R gene inserted in frame 7 base pairs downstream of the 5' AUG for the 39K gene. This plasmid was derived from p39CATQ- (L. A. Guarino and M. D. Summers, *J. Virol.*, 57:563–471 (1986a)) by digestion with BstBI, followed by repair with the Klenow fragment of DNA polymerase I, deletion of the CAT sequences with BamHI, and insertion of the BglII (repaired)-BamHI fragment encoding Neo-R at the BstBI and BamHI sites. According to the preferred embodiment of this invention, the AcMNPV transcriptional enhancer element hr5 may be utilized. However, those skilled in the art who have the benefit of this disclosure will recognize that other transcriptional enhancer elements may also be suitably utilized in combination with a baculovirus early gene or gene promoter. In particular, it is expected that at least the AcMNPV transcriptional enhancer elements hr1, hr2, hr3 and hr4 described and characterized in L. A. Guarino, M. A. Gonzalez and M. D. Summers, *J. Virol.*, 60:224–229 (1986) may be utilized to advantage.

The plasmid p39E-Neo was constructed in similar fashion to the plasmid p39E+Neo. However, p39-Neo lacks the hr5 (or other) enhancer, and is constructed by HindIII digestion and religation of p39E+Neo.

The plasmid pIE139Neo was derived from p39CAT-/IE-1 (L. A. Guarino and M. D. Summers, *J. Virol.*, 57:563–571 (1986a)) by replacing the BamHI CAT fragment with the BolII-BamHI fragment encoding Neo-R.

The plasmid p510Neo was constructed by inserting the BglII-BamHI fragment encoding Neo-R at the unique BamHI site of pAc510, a late transfer vector described previously by M. D. Summers and G. E. Smith, *A Manual of Methods for Baculovirus Vectors and Insect Cell Culture Procedures*, Texas Agricultural Experiment Station Bulletin No. 1555, Texas A&M University, (1987).

The plasmid pIE1FB was constructed by adding a BglII linker at the Eco47III site of pAcIE1, then inserting a BglII fragment from pDP500 (D. Panicali, A. Grzelecki and C. Huang, *Gene*, 47:193–199 (1986)), which encodes a functional *E. coli* β-galactosidase, at that site. This positions the β-galactosidase gene in frame at a site 36 base pairs downstream of the translational start site for IE1, fusing the first 12 amino acids of IE1 with the β-galactosidase fragment.

The plasmid pIE1NFB was constructed in similar fashion to the pIE1FB construct, except the BglII fragment encoding β-galactosidase was inserted 39 base pairs upstream of the IE1 translational start site, at HincII, so that this plasmid encodes a nonfused β-galactosidase gene product.

The plasmid p39E+FB was analogous in construction to p39E+Neo, except it contains the β-galactosidase coding sequence in place of the Neo-R coding sequence.

The plasmid pIE1tPA was analogous in construction to pIE1FB, except the BamHI fragment encoding tissue plasminogen activator (tPA) was inserted 36 base pairs downstream of the IE1 translational start site, instead of β-gal, and it is out-of-frame with respect to the IE1 coding sequence. Thus, this plasmid encodes a nonfused tPA gene product.

Additionally, those skilled in the art who have the benefit of this disclosure will recognize that other plasmids can be prepared utilizing other heterologous genes of interest and other baculovirus early promoters.

EXAMPLE II

Construction of Stably-Transformed Insect Cell Clones

To construct a stably-transformed insect cell clone according to the present invention, a clonal derivative of the Lepidopteran insect cell line, designated Sf9, is used to generate stable genetic variants containing one or more of the novel genetic constructions described above. Sf9 cells were seeded at a density of about $1 \times 10^6$ in 35 mm culture dishes and allowed to attach for at least one hour. The medium was removed, then the cells were cotransfected with a mixture of 2 μg of the plasmid containing heterologous DNA coding for a desired protein (e.g. β-galactosidase) and 1 μg of pIE1Neo DNA, using established methods set forth in M. D. Summers and G. E. Smith, *A Manual of Methods for Baculovirus Vectors and Insect Cell Culture Procedures,* Texas Agricultural Experiment Station Bulletin No. 1555, Texas A&M University, (1987).

After transfection, the cells were incubated for 2 hours at 28° C., washed, and fed with TNMFH medium (M. D. Summers and G. E. Smith, (1987), *supra;* W. F. Hink, *Nature (London),* 226:466–467 (1970)) supplemented with 10% fetal calf serum (Hazelton Research Products, Inc., Lenexa, Kansas) and antibiotics (complete TNMFH). The cells were incubated for another 22 hours at 28° C., then each dish was subcultured at low cell density to generate multiple sparsely-seeded 60 mm culture dishes. Each 60 mm culture dish was typically seeded with approximately $5 \times 10^4$ cells. These were incubated for another 24 hours at 28° C., then the medium in each dish was replaced with fresh complete TNMFH containing 1 mg of the neomycin antibiotic, G418, (GIBCO; Grand Island, New York) per ml. The cultures were incubated at 28° C. for 1 week, the medium was replaced, and the cultures were incubated at 28° C for another week. The medium then was replaced with complete TNMFH lacking G418 and the cultures were incubated at 28° C. until colonies were clearly visible to the naked eye. At that time, individual colonies were picked, and each was amplified until large enough numbers of cells were available for analysis. Once amplified, clones of interest were routinely grown at 28° C. in complete TNMFH, either as adherent or as suspension cultures.

EXAMPLE III

Evaluation of Promoters for Use in Continuous Expression of Heterologous Genes AcMNPV immediate-early and delayed-early promoters are exemplified by the IE1 and 39K promoters, respectively. However, those skilled in the art who have the benefit of this disclosure will recognize that other baculovirus early promoters may be utilized to advantage. The ability of these viral promoters to drive the constitutive expression of the antibiotic resistance Neo-R gene in stably-transformed Sf9 cells was established.

Sf9 cell cultures were transfected with different plasmids as constructed according to Example I (i.e., pIE1Neo, p39E− Neo, p39E+Neo, pIE139Neo, p510Neo, pIE1FB, pIE1NFB, p39E+FB, pIE1tPA), washed, and incubated for 24 hours at 28° C. These cell cultures were then subcultured to produce 24 plates (60 mm diameter) seeded with equal numbers of cells. Twelve of the plates from each culture were seeded with cells in fresh TNMFH, while the other 12 were seeded in fresh TNMFH containing 1 mg of the antibiotic G418 per ml. To establish the number of cells initially seeded into each dish, viable cell counts were performed on triplicate samples of the starting cell suspensions, using the standard trypan blue exclusion staining techniques as described in M. D. Summers and G. E. Smith, *A Manual of Methods for Baculovirus Vectors and Insect Cell Culture Procedures,* Texas Agricultural Experiment Station Bulletin No. 1555, Texas A&M University (1987). Subsequently, triplicate plates were counted either at 2- or 4-day intervals, for either control- or G418-treated cells, respectively.

Regardless of the plasmid used for transfection, all of the cells had approximately equivalent growth curves in the absence of the antibiotic G418. Moreover, these growth curves were typical of normal, untransfected Sf9 cells. This indicated that none of the plasmids had a severely toxic effect over the time period studied. In the presence of the antibiotic G418, cells that were transfected with p510Neo did not survive. This result was consistent with the idea that expression of the Neo-R gene from the very late polyhedrin promoter requires the previous expression of a number of other viral genes (L. K. Miller, *Annual Review of Microbiol.,* 42:177–199 (1988)) which were absent in these cells. In contrast, large numbers of G418-resistant cells were obtained when Sf9 cells were transfected with pIE1Neo or p39E+Neo plus pIE1. These results show that either the IE1 promoter or the 39K promoter can be used to continuously express the Neo-R gene product in Sf9 cells. It should be noted that these promoters, and other baculovirus early promoters could drive the continuous expression of other heterologous gene products, as well, such as, β-galactosidase, tissue plasminogen activator, human interleukin-2, and human β-interferon, for example. It should also be noted that other antibiotic-resistance genes, such as those encoding resistance to hygromycin B or methotrexate could be used to advantage in addition to those encoding resistance to neomycin.

The results also established the influence of the IE1 gene product and the exemplary transcriptional enhancer element, hr5 (L. A. Guarino and M. D. Summers, *J. Virol.,* 60:215–223 (1986b); L. A. Guarino, M. A. Gonzalez and M. D. Summers, *J. Virol.,* 60:224–229 (1986)), on continuous gene expression from the 39K promoter. The smallest numbers of G418-resistant cells were obtained by transfection with p39E−Neo in the absence of IE1. Transfection with p39E−Neo in the presence of IE1 or with p39E+Neo in the absence of IE1 produced larger numbers of G418-resistant cells. The largest numbers were obtained in the presence of both IE1 and hr5. These results are in agreement with the results of previous transient expression assays, which have established that expression from the 39K promoter is activated in trans by the IE1 gene product and in cis by hr5 (L. A. Guarino and M. D. Summers, *J. Virol.,* 57:563–571 (1986a); *J. Virol.,* 60:215–223 (1986b)). Interestingly, approximately equivalent numbers of resistant cells were obtained by using either the IE1 promoter alone or the 39K promoter in the presence of both IE1 and hr5. Based upon these observations, either the IE1 promoter alone or the 39K promoter in the presence of IE1 and the AcMNPV transcriptional enhancer element hr5 are equally effective as promoters for the production of stably-transformed Sf9 cell variants capable of continuous foreign gene expression. It should also be noted that in addition to hr5, the AcMNPV transcriptional enhancer elements hr1, hr2, hr3 and hr4 could be utilized to advantage.

EXAMPLE IV

Construction of Stably-transformed Sf9 Cells Expressing E. coli β-galactosidase from Baculovirus Early Gene Promoters To generate stably-transformed variants that continuously express *E. coli* β-galactosidase, Sf9 cells were cotransfected with the plasmids of Example I as follows: pIE1FB plus pIE1Neo, pIE1NFB plus pIE1Neo, or p39E+FB plus pIE1 and pIE1Neo. After cotransfection, G418-resistant cells were selected, and colonies were isolated as described in Examples I-III. Well-isolated colonies were picked and amplified. Cytoplasmic extracts were then prepared from the individual clones and assayed for β-galactosidase activity (Table 1). β-galactosidase activity was detected in over one-half of the clones isolated after transfection with IE1FB or IE1NFB and in more than one-third of those isolated after transfection with p39E+FB. The clone designated IE1FB2 had the highest activity, which was about 5-15% of that transiently expressed in Sf9 cells infected for 24 hours with Ac360-βgal or VL720-βgal. Ac360-βgal and VL720-βgal are recombinant baculoviruses in which transient expression of the β-galactosidase gene is driven by the polyhedrin promoter (See M. D. Summers and G. E. Smith, *A Manual of Methods for Baculovirus Vectors and Insect Cell Culture Procedures*, Texas Agricultural Experiment Station Bulletin No. 1555, Texas A&M University (1987), regarding Ac360-βgal and V. A. Luckow and M. D. Summers, *Virol.*, 167:56-71 (1988b), regarding VL720-βgal). Further analysis showed that three of the four positive IE1FB clones expressed β-galactosidase continuously for at least 29 passages in culture (Table 2). The clone IE1FB2 expressed β-galactosidase activity continuously for over 55 passages, as shown in Table 2. The IE1FB5 clone, which lost the ability to express β-galactosidase, lacked integrated plasmid DNA sequences after about 20 passages. These results indicated that the IE1FB cells, in general, expressed less β-galactosidase after about 55 passages than after 3-4 passages. However, the level of expression stabilized by passage number 30, evidencing that continuous expression of a foreign gene was achieved in a stably-transformed cell line.

TABLE 2

Effect of passage on β-gal activity.

| Clone/Passage | β-Gal −U/106 Cells |
|---|---|
| IE1FB1 p4 | 0.000 |
| IE1FB1 p31 | 0.000 |
| IE1FB2 p4 | 0.479 |
| IE1FB2 p23 | 0.092 |
| IE1FB2 p31 | 0.134 |
| IE1FB2 p55 | 0.128 |
| IE1FB4 p4 | 0.021 |
| IE1FB4 p30 | 0.016 |
| IE1FB5 p4 | 0.079 |
| IE1FB5 p29 | 0.000 |
| IE1FB7 p3 | 0.025 |
| IE1FB7 p29 | 0.004 |

To verify the presence of β-galactosidase-related polypeptides in the transformed Sf9 cell clones, the cells were pulse-labeled, detergent-extracted, and the immunoprecipitates were analyzed by SDS-PAGE. The pIE1FB-transformed clones 2, 4 and 7 described here each contained a specifically immunoreactive polypeptide with an apparent molecular weight of about 120,000. This polypeptide was not detected in mock- or AcMNPV-infected Sf9 cells or in the IE1FB-transformed clones 1 or 5 (note that clone 5 was initially positive, but reverted with passage; Table 2). This polypeptide comigrated with a similar recombinant product expressed by Ac360-βgal, in which the first 11 amino acids of polyhedrin were fused in frame to β-galactosidase (M. D. Summers and G. E. Smith, *A Manual of Methods for Baculovirus Vectors and Insect Cell Culture Procedures*, Texas Agricultural Experiment Station Bulletin No. 1555, Texas A&M University (1987)). Thus, by the criteria of specific immunoreactivity, molecular size, and enzymatic activity, the polypeptide produced by the procedures described herein represented the authentic IE1-β galactosidase fusion product.

A comparison of the relative amounts of the β-gal synthesized by the different Sf9 cell transformants in a 4-hour labeling period revealed that the IE1FB2 clone produced the largest amount of β-gal. On the average, the IE1 fusion constructs (IE1FB) expressed larger amounts of β-gal than the nonfused IE1 (IE1NFB) constructs, and the 39K constructs (39FB) expressed less than the IE1 constructs. Significantly higher amounts of β-gal were labeled in Sf9 cells infected sta-

TABLE 1

β-gal activity in extracts of stably-transformed Sf9 clones

| Clone | β-Gal −U/106 Cells | Clone | β-Gal −U/106 Cells | Clone | β-Gal −U/106 Cells |
|---|---|---|---|---|---|
| IE1FB1 p4 | 0.000 | IE1NFB1 p3 | 0.000 | 39 E + FB1 p1 | 0.000 |
| IE1FB2 p4 | 0.479 | IE1NFB2 p2 | 0.012 | 39 E + FB2 p1 | 0.000 |
| IE1FB4 p4 | 0.021 | IE1NFB3 p3 | 0.002 | 39 E + FB3 p1 | 0.015 |
| IE1FB5 p4 | 0.079 | IE1NFB4 p2 | 0.011 | 39 E + FB4 p1 | 0.001 |
| IE1FB6 p3 | 0.001 | IE1NFB5 p1 | 0.030 | 39 E + FB5 p1 | 0.000 |
| IE1FB7 p3 | 0.025 | IE1NFB6 p2 | 0.002 | 39 E + FB6 p1 | 0.000 |
| IE1FB8 p3 | 0.000 | IE1NFB7 p1 | 0.011 | 39 E + FB7 p1 | 0.000 |
|  |  | IE1NFB8 p1 | 0.054 | 39 E + FB8 p1 | 0.005 |
|  |  | IE1NFB9 p1 | 0.022 | 39 E + FB9 p1 | 0.003 |
| Sf9 | 0.000 | IE1NFB10 p3 | 0.030 | 39 E + FB14 p3 | 0.003 |
| Sf9/720βGal |  | IE1NFB11 p3 | 0.158 | 39 E + FB16 p3 | 0.001 |
| Undiluted | 4.390 | IE1NFB12 p3 | 0.018 | 39 E + FB17 p3 | 0.001 |
| 1:10 | 0.920 |  |  | 39 E + FB18 p2 | 0.004 |
| 1:100 | 0.275 |  |  | 39 E + FB20 p2 | 0.000 |
| Sf9/360βGal |  |  |  | 39 E + FB21 p2 | 0.011 |
| Undiluted | 3.585 |  |  | 39 E + FB22 p3 | 0.000 |
| 1:10 | 0.372 |  |  |  |  |
| 1:100 | 0.008 |  |  |  |  | bly-transformed cells. This reflects a much higher rate of β-gal synthesis in the infected cells during the four hour labeling period. Curiously, IE1FB2 cells at a higher passage level (P41) actually produced more radiolabeled β-gal during the four hour labeling period than the same cells at a lower passage level (P8).

Immunofluorescence microscopy was performed to examine the intracellular distribution of β-galactosidase in the IE1FB2 cells. Normal Sf9 cells were not stained, while VL720-β-gal infected Sf9 cells exhibited intense cytoplasmic fluorescence. Although the reaction is much less intense, a similar distribution of fluorescence was observed in IE1FB2 cells. Phase microscopy revealed that the overall morphology of IE1FB2 cells is quite similar to that of Sf9 cells Western blotting analysis was performed to examine the total amounts of β-gal that accumulated in each clone in 24, 48, or 72 hours of growth. The results verified that there was significantly less β-gal in the stably-transformed cells than in the transient BEV infected cells at corresponding times post-infection (note that tenfold less of the infected cell extracts was loaded in each case). The amounts of β-gal produced by IE1FB2 at various passage levels were compared to serial dilutions of an extract from the transient BEV 360-βgal-infected cells. The amount of β-galactosidase produced the IE1FB2 clone was higher than that produced in Sf9 cells transfected with pIE1FB DNA, but it was significantly lower than the amount produced between 20-24 hours post infection in Sf9 cells infected with the Ac360-βgal transient BEV system. The relative amounts of β-galactosidase labeled during the 4 hour pulse of each cell type was determined by excising the β-galactosidase bands, solubilizing the gel slices, and counting the radioactivity. After 48 hours of growth, IE1FB2 contained about 0.1-0.5% of the total β-gal-related protein in Sf9 cells infected for 48 hours with 360-βgal in a transient BEV system. Similar amounts of β-gal were detected in IE1FB2 at different passage levels, ranging from P23 to P55. Finally, both immunoprecipitation and western blotting revealed that the transient BEV infected cell extracts contained large amounts of numerous β-gal-related polypeptides smaller than the intact β-gal product. Thus, while the transient BEV infected cells produce significantly larger amounts of β-gal than the stably-transformed cells of this invention, the product from the transient BEV system is contaminated with relatively larger amounts of what are probably degradation products, even at relatively early times (24 hours) post-infection.

Genetic Analysis

Genetic analysis of β-gal expression in Sf9 cells transformed with IE1-β-gal constructs was performed to verify that the heterologous DNA sequence encoding for the foreign gene (here β-galactosidase) was stably integrated into the host cell chromosome. Total cellular DNA was extracted from Sf9 cells or from various IE1FB clones and digested with EcoRI. The digests were resolved by gel electrophoresis, transferred to nitrocellulose filters, and the filters were hybridized with radiolabeled pIE1FB probes as described in Examples I-III. Plasmid-specific sequences were detected in the DNA isolated from IE1FB clones 2, 4, and 7, but not from Sf9 cells or IEIFB clones 1 or 5. These pIEIFB-specific sequences were present in significantly higher copy number in the DNA from IEIFB2 as compared to IE1FB clones 4 and 7; these contained approximately equivalent amounts of plasmid specific DNA, but much less than IE1FB2. Thus, the relative amounts of plasmid-specific DNA corresponded to the relative levels of β-galactosidase activity expressed by these clones.

The results obtained also suggest that the loss of β-gal activity in IE1FB5 (positive at P4 but negative at P29; Table 2) resulted from loss of the pIE1FB-related sequences at some point prior to P19. In contrast, IE1FB2 DNA still contained significant amounts of pIEIFB-related sequences at P55, indicating that these sequences are maintained stably in this clone. The Southern blots of total cellular DNA suggest that pIE1FB is integrated in IE1FB clones 2, 4 and 7. The plasmid-specific DNA in IE1FB7 occurs primarily as offsize restriction fragments. Moreover, offsize restriction fragments also are detectable in IE1FB2 and IE1FB4 DNA in longer exposures of the autoradiograms. However, the hybridization patterns of the latter two clones suggest that they contain tandem repeats of the integrated plasmid DNA. Finally, the multiple offsize restriction fragments detected in DNA from IE1FB2 suggests that the plasmid may be integrated at several sites in this clone.

S1 nuclease protection assays were performed to determine if the pIE1FB-related sequences integrated in the IE1FB clones were transcribed. Total cellular RNA was extracted from the cells at passage 18 and S1 mapping was carried out with 5' end-labeled pIE1Neo and pIE1FB fragments as probes. A 168 base pair fragment of the pIE1Neo probe was protected by RNA from each of the IE1FB clones, but not by RNA from untransformed Sf9 cells. This shows that the antibiotic resistance Neo-R gene is transcribed in each of the IE1FB clones, a result which is corroborated by their ability to survive in the presence of the antibiotic G418. It also shows that transcription initiates specifically within the IE1 promoter. A 293 base pair fragment of the pIE1FB probe was protected by RNA from IE1FB2 and IE1FB4, but not by RNA from untransformed Sf9 cells or from IE1FB1, IE1FB5, or IE1FB7.

Again, this shows that the integrated sequences are transcribed and that transcription initiates specifically within the IE1 promoter. Moreover, the relative amounts of RNA expressed in the different IE1FB clones, revealed by the degree of nuclease protection, corresponded closely with the amounts of β-gal fusion protein produced. This suggests that the differences observed in the relative amounts of βgal produced by the various IE1FB clones depend upon differences in the total levels of transcription of the integrated plasmid DNA sequences.

EXAMPLE V

Construction of Stably-Transformed Sf9 Cells Continuously Expressing Human Tissue Plasminogen Activator from the IE1 Promoter Using the methods detailed in Examples I-IV, stably-transformed variants were constructed which continuously express human tissue plasminogen activator (tPA). In similar fashion to Example IV, Sf9 cells were cotransfected with pIE1tPA plus pIE1Neo. After transfection, G418-resistant cells were selected, and colonies were isolated as described in Examples I-III. Well-isolated colonies were picked and amplified. Similar to Example IV, to verify the presence of tPA related polypeptides in the transformed Sf9 cell clones, the cells were pulse-labeled, detergent-extracted, and immunoprecipitates were analyzed by SDS-PAGE. Several of the clones expressed a polypeptide which, by the criteria of immunoreactivity and molecular size was identical to authentic tPA. The pIE1tPA-transformed clones expressed significantly less activity than that expressed in Sf9 cells infected for 24 hours with 941-tPA. 941-tPA is a recombinant baculovirus in which expression of the tPA gene is driven by the polyhedrin promoter in a transient BEV system. (See D. L. Jarvis and M. D. Summers, *Mol. Cell. Biol.*, 9:214–223 (1989)).

Although the amount of tPA expressed by the stably-transformed cell line was less than the amount expressed by the BEV system, the amount of tPA secreted was virtually identical in both systems. Significantly, almost all of the tPA expressed in the stably-transformed cell lines was secreted, indicating that the ability of the transformed cell to process newly synthesized proteins remained unaltered. In direct contrast, only a small fraction of the tPA expressed by the BEV system was secreted due to the late viral effects adversely impacting the cell's ability to process the foreign gene product.

EXAMPLE VI

Detailed Description of the Immediate Early Transfer Vector (IETV)

FIG. 2 diagrams the immediate early transfer vector (pIETV). pIETV is constructed from the EcoRI fragment of AcNPV DNA. Parenthesis indicate sites destroyed during construction. Arrows indicate direction of transcription of the indicated genes; arrow heads indicate poly- adenylation sites. The shaded box indicates the location of a multiple cloning site sequence (sequence shown in the lower portion of FIG. 2.)

The plasmid contains the promoters from baculovirus IE1 and IEN genes positioned in opposite orientations at the Eco RV site, which is located about 100 bp upstream of the polyhedrin translational start site (FIG. 2). A cloned copy of the *E. coli* lac Z gene, encoding enzymatically active $\beta$-galactosidase, is inserted immediately 3' of the IEN promoter. Because the IEN promoter belongs to the immediate early class, this plasmid will express $\beta$-galactosidase in uninfected insect cells or, once incorporated into a recombinant baculovirus, during the immediate early phase of infection.

The expression of $\beta$-galactosidase allows one to quickly and easily identify insect cell transformants or recombinant viruses containing the plasmid DNA sequences, as it will produce a blue color when incubated with a chromogenic substrate. The IEN-$\beta$-gal gene is flanked on the 3' side by a polyadenylation site and the noncoding sequences normally found on the 5' side of the polyhedrin promoter. On the other side of the IEN-$\beta$-gal gene is the IE1 promoter, positioned in opposite orientation. A multiple cloning site (MCS) is inserted immediately after the first nucleotide of the IE1 translational initiation codon. The MCS contains several unique restriction endonuclease sites for the insertion of foreign genes.

Like the lac Z gene, the foreign gene insert is expressed in uninfected insect cells or, once incorporated into a recombinant virus, it is expressed during the immediate early phase of viral infection. The sequences on the 3' side of the MCS include the IE1 polyadenylation site, followed by the polyhedrin promoter, the intact polyhedrin coding sequence, and 3' noncoding sequences normally found on the 3' side of the polyhedrin gene.

The sequences that flank the two early promoters are specifically included for three reasons:
  (1) The polyadenylation sites provide signals for the processing of transcripts.
  (2) The other noncoding sequences target the plasmid DNA to the polyhedrin locus of wild-type baculovirus DNA where the plasmid sequences can be inserted into the viral genome by homologous recombination.
  (3) Because both the polyhedrin promoter and the polyhedrin coding sequences are included, the recombinant viruses can produce occluded progeny virions. This feature makes these recombinants ideal for the infection of insects, as occluded virus is more highly infectious in vivo and is more resistant to environmental inactivation, as compared to nonoccluded recombinant viruses.

EXAMPLE VII

Figure 3:
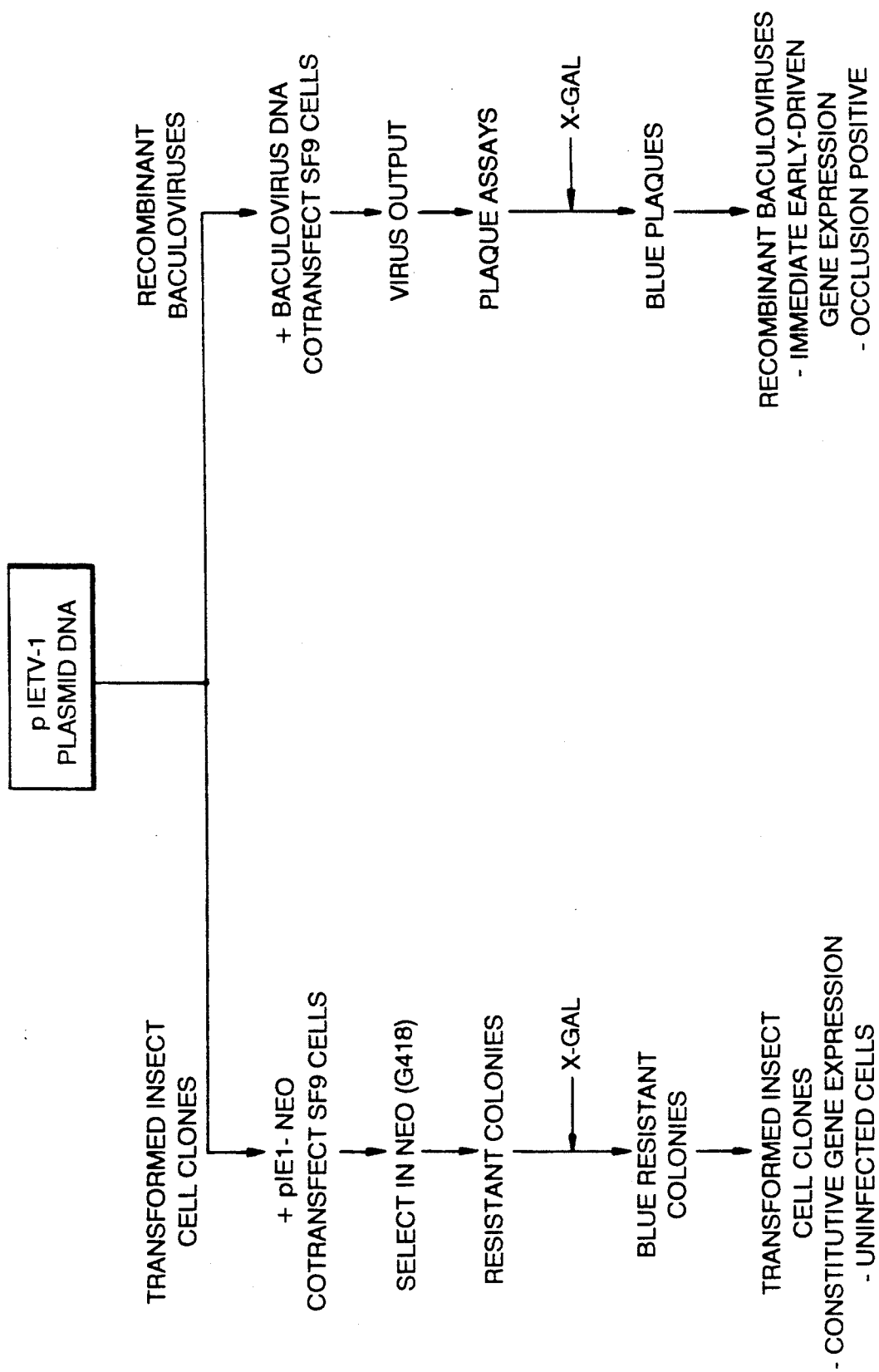
FIG. 3 diagrams using the immediate early transfer vector plasmid DNA (pIETV) and two different methods to generate either transformed insect cell clones or recombinant baculoviruses.

IETV Transfer Plasmid Vector Use for Transient or Stable Foreign Gene Expression FIG. 3 diagrams the use of the immediate early transfer vector plasmid DNA (pIETV) with two different methods to generate either transformed insect cell clones or recombinant baculoviruses.

This improved plasmid vector can be used to produce either insect cell transformants or recombinant baculoviruses. This vector permits the expression of a foreign gene either in uninfected insect cells or during the immediate early phase of infection in insect cells or in insects. This improved plasmid includes a marker gene for quick and easy identification of the desired transformed cell clones over recombinant viruses. The vector also includes a multiple cloning site to facilitate the insertion of the foreign gene that one wants to express.

Recombinant viruses constructed using these vectors can produce occluded progeny virions. This capability, which is lacking in recombinant baculoviruses designed in other ways, allows one to infect insects and achieve foreign gene expression in vivo during the early stages of infection. Recombinant viruses produced from this improved vector are capable of synthesizing polyhedrin. Therefore, they will produce occluded progeny that are highly infectious in vivo and will resist environmental inactivation. These properties are particularly critical for the expression of foreign gene products, including insecticides, in insects.

As shown in FIG. 3, the improved plasmid vector (pIETV-1) allows for the expression of desired genes in either transformed insect cell clones or recombinant baculoviruses.

In general, the following are steps performed to produce TRANSFORMED INSECT CELL CLONES:
  1. 2 $\mu$g the plasmid pIETV-1 DNA is co-transfected with 1 $\mu$g pIE1-NEO DNA into SF9 cells. The cells are allowed to recover overnight, then seeded at low density;
  2. Cells containing the NEO gene are selected in medium containing 1 $\mu$g/ml G418. After two weeks in the G418 containing medium, several individual clones are picked and transferred to single wells in a 24-well plate;
  3. X-gal is added to the wells. Wells displaying a blue color contain cells that incorporated the NEO gene as well as the IEN-β-gal gene. Transformants that are NEO positive and β-gal positive will have constitutive gene expression of the desired gene that was transfected along with the β-gal gene as part of the IETV construct. The desired gene of choice is then produced in the necessary quantities and then isolated using standard techniques known to those skilled in the art of gene expression and protein purification.

The above steps are essentially identical to those described in Example II and IV for producing cell lines with NEO selection.

Briefly, RECOMBINANT BACULOVIRUSES are produced in the following manner (See Example VIII for detailed description):

1. 2 μg plasmid DNA (pIETV-1) is cotransfected with 1 μg baculovirus DNA into SF9 cells; medium is harvested and clarified 3–5 days later, viral clones are isolated by plaque assay.
2. Virus is generated;
3. Blue plaques (recombinant viruses) are identified by adding an agarose overlay containing X-gal;
4. Recombinant viruses are isolated. Individual isolates are tested for ability to express the desired gene early after infection and that are also occlusion positive.

EXAMPLE VIII

Detailed Description of Producing a Recombinant Virus With the IETV Without an Insert Behind IE1 Promoter All methods for construction, characterization, isolation and purification of baculovirus vectors and baculoviral DNA as well as insect cell culture procedures are known to those skilled in this art and are outlined in *A Manual of Methods for Baculovirus Vectors and Insect Cell Culture Procedures* (Summers, M. D. and G. E. Smith, TAES Bulletin No. 1555, 1988). Homologous recombination, plaque selection, purification and propagation procedures as well as cotransfection protocols are known to those familiar and skilled in this art (same as above).

Bacterial transformation, screening by restriction mapping, extraction, construction of bacterial transfer vectors, purification of bacterial plasmid DNA, as well as other standard molecular biology procedures, will be accomplished by standard recombinant DNA techniques (Maniatis, et al, *Molecular cloning: A laboratory manual*, Cold Spring Harbor Press, Cold Spring Harbor, NY (1982)).

Standard recombinant procedures are used for the construction of recombinant plasmids (Maniatis et al , 1982) as well as for the generation and propagation of recombinant baculovirus strains (Summers and Smith, 1987).

In general, recombinant baculovirus is obtained by cotransfection of Sf9 cells with wild-type baculovirus DNA and transfer vector plasmid DNA containing the β-galactosidase gene. The next step involves the selection of blue viral plaques because recombinant baculoviruses containing the β-galactosidase gene produces blue plaques and is therefore easy to isolate by the standard plaque assay (Summers and Smith, 1987). Once the viral blue plaques are identified, the recombinant baculovirus is isolated, purified and propagated by techniques known to those skilled in this art.

Cloning of the β-galactosidase gene adjacent to the early IEN gene promoter will be briefly presented herein. This baculovirus transfer vector, in addition to containing the early IE1 gene promoter, will contain viral flanking sequences which are necessary for the production of viral recombinants through homologous recombination at the polyhedrin locus. A Sma 1 - Pst 1 fragment from pMC1871 (Shapira, et al, Gene 25:71–82 (1983)) will be cloned into the transfer vector 3' to the early IE1 gene promoter. This pMC1871 Sma 1 -Pst 1 fragment contains the sequences encoding the β-galactosidase gene (starting at amino acid 9 and proceeding through its natural termination site).

The details of the selection process involving homologous recombination and standard plaque assay procedures are known to those skilled in the art but a brief description of them will be presented herein. The Sf9 clone of the IPLB-Sf21 AE cell line will be used in these experiments (derived from Spodoptera frugiperda: Vaughn, et al In Vitro 13:213–217 (1977)). Individual Sf9 cell cultures will be cotransfected with wild type baculovirus DNA plus IETV (IE1-β-galactosidase) bacterial plasmid DNA.

At about 5 days post-transfection, the growth medium will be harvested, clarified and used for plaque assays on fresh Sf9 cell monolayers. Assuming that the added IE1 sequence does not inactivate β-gal activity, the β-gal portion of the plasmid should therefore remain enzymatically active. The chromogenic substrate 'x-gal' (Promega-Biotech), which turns blue when it reacts with β-gal, will be added to the agarose overlay in these plaque assays. Recombinant viral plaques will be identified on the basis of their blue color. The blue plaques will be isolated, plaque purified, and the working virus stocks will be prepared in Sf9 cells and stored using standard methods (Step G: Summers and Smith, TAES Bull. 1555 (1987)).

EXAMPLE IX

Cloning β Galactosidase and β Glucuronidase Under the Control of IEN Promoter and IE1 promoter, Respectively The pIETV construct described herein is useful to test the expression of any two different genes. For example, the bacterial gene β-glucuronidase (GUS) may be cloned into the Pst1 sites of pIETV. The GUS gene is then under the direct control of IE1 promoter. GUS is similar to βgal because its expression can be easily monitored using chromogenic substrates. GUS therefore is used as an additional test gene. Viral recombinants or stable cell lines can be produced as described above. The expression of βgal is now under the control of an IEN promoter, and the expression of GUS is under the control of an IE1 promoter.

EXAMPLE X

Cloning β Galactosidase And Tissue Plasminogen Activator Under the Control of IEN Promoter and IE1 Promoter, Respectively Virtually any desired gene may be placed under the control of the IE1 promoter in the pIETV vector. The desired gene is chosen on the basis of need for expressing such a gene or the desired gene could allow the investigator to study a specific related aspect. For example, tissue plasminogen activator (tPA) can be cloned into the pIETV vector. The cells containing β galactosidase are then be selected for recombinant viral production or for generation of a transformed cell line. Selection would utilize the βgal marker system as described above. tPA would be of special interest in terms of studying processing of the protein itself. The inventors predict that the results from this experiment would be similar t results obtained when studying tPA, in stable cells, under control of IE1. In stable cell lines, under IE1 control, tPA is efficiently processed. However, in infected cells, under polyhedrin control, tPA is not optimally expressed or processed.

While the compositions and methods of this invention have been described in terms of preferred embodiments, it will be apparent to those of skill in the art that variations and modifications may be applied to the composition, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. The method outlined in the Examples presented supra describe the methods for producing stably transformed cell lines that continuously and permanently express a desired gene. The Examples also detail a novel vector that allows for the generation of either transformed insect cell clones or recombinant baculoviruses. This invention allows for potential production of human, animal or plant proteins either on a long term or transient basis. All such similar substitutes and modifications apparent to those skilled in the art are deemed to be within the spirit, scope and concept of this invention as defined by the appended claims.

What is claimed is:

9. A transformed insect cell clone comprising the baculovirus vector of claim 1 and a DNA sequence encoding a structural gene for a heterologous protein positioned at the cloning restriction site.

10. The transformed insect cell clone of claim 1 which is a stably transformed insect cell clone.

11. The transformed insect cell clone of claim 9 which is a Lepidopteran insect cell clone selected from the group of Lepidopteran insects consisting of *Spodoptera frugiperda, Bombyx mori, Heliothis virescens, Heliothis zea, Mamestra brassicas, Estigmene acrea* or *Trichoplusia ni.*

12. The transformed cell clone of claim 11 which is from cell line Sf9.

15. A baculovirus expression system comprising Lepidopteran insect cells stably transfected or transiently infected with a baculovirus vector comprising the following components directionally positioned from left to right:
(a) a 5' end flanking baculovirus viral DNA for baculoviral recombination;
(b) DNA consisting essentially of a first baculovirus immediate early gene promoter;
(c) DNA consisting essentially of a structural gene for a selectable marker gene positioned upstream and in frame to said DNA sequence encoding the first promoter, wherein the first promoter mediates the transcriptional expression of said selectable marker gene;
(d) DNA consisting essentially of a second baculovirus immediate early gene promoter positioned in the opposite orientation to the first promoter;
(e) DNA consisting essentially of a cloning restriction site for insertion of a cDNA sequence encoding a heterologous protein;
(f) DNA encoding a structural gene for a heterologous protein inserted at the cloning restriction site;
(g) DNA consisting essentially of a polyhedrin gene; and
(h) a 3' end flanking baculovirus viral DNA for baculoviral recombination.

17. The baculovirus expression system of claim 15 wherein the first or second promoter is the baculovirus immediate early gene IE1 or the baculovirus immediate early gene IEN.

18. The baculovirus expression system of claim 15 further comprising DNA coding a baculovirus delayed-early gene promoter from the 39K delayed-early gene and the hr5 enhancer.

19. The baculovirus expression system of claim 15 wherein the selectable marker gene encodes beta-galactosidase, beta-glucuronidase, or chloramphenicol acetyltransferase.

20. The baculovirus expression system of claim 15 wherein the Lepidopteran insect cells are selected from the group of Lepidopteran insects consisting of *Spodoptera frugiperda, Bombyx mori, Heliothis virescens, Heliothis zea, Mamestra brassicas, Estigmene acrea* or *Trichoplusia ni.*

1. A baculovirus vector comprising the following components directionally positioned from left to right:
(a) DNA consisting essentially of a first baculovirus immediate early gene promoter:
(b) DNA consisting essentially of a second baculovirus immediate early gene promoter positioned in the opposite orientation to the first promoter; and
(c) DNA consisting essentially of a cloning restriction site for insertion of a DNA sequence encoding a heterologous protein.

2. The baculovirus vector of claim 1 further including a DNA sequence encoding a structural gene for a selectable marker gene positioned upstream and in frame to the DNA sequence encoding the first promoter, wherein the first promoter mediates the transcriptional expression of said marker gene.

3. The baculovirus vector of claim 1 wherein the cloning restriction site comprises a DNA encoding a multiple cloning cassette positioned downstream and in frame to the first nucleotide of the second promoter.

4. The baculovirus vector of claim 1 further including DNA encoding a structural gene for a heterologous protein positioned at the cloning restriction site and in frame with the second promoter, whereby the second promoter mediates the transcriptional expression of the heterologous protein.

5. The baculovirus vector of claim 1 wherein the selectable marker gene encodes betagalactosidase, beta-glucuronidase, or chloramphenicol acetyltransferase.

6. The baculovirus vector of claim 1 wherein the first or second promoter is from baculovirus immediate early gene IE1 or baculovirus immediate early gene IEN.

7. The baculovirus vector of claim 1 further comprising DNA coding a baculovirus delayed-early gene promoter from the 39K delayed-early gene and the hr5 enhancer.

8. The baculovirus vector of claim 1 wherein the first or second promoter is from the viral DNAs of *Autographa californica* NPV, *Trichoplusia ni* NPV, *Rachipulsia ou* NPV, *Orgyia psuedosugata* NPV, *Bombyx mori* NPV, *Heliothis zea* NPV, *Spodoptera exigua* NPV or *Galleria mellonella* NPV.

13. A baculovirus vector comprising the following components directionally positioned from left to right:
  (a) a 5' end flanking baculovirus viral DNA for baculoviral recombination;
  (b) DNA consisting essentially of a first baculovirus immediate early gene promoter;
  (c) DNA consisting essentially of a second baculovirus immediate early gene promoter positioned in the opposite orientation to the first promoter;
  (d) DNA consisting essentially of a cloning restriction site for insertion of a DNA sequence encoding a heterologous protein;
  (e) DNA consisting essentially of the polyhedrin gene; and
  (f) a 3' end flanking baculovirus viral DNA for baculoviral recombination.

14. The baculovirus vector of claim 13 further including DNA encoding a structural gene for a heterologous protein positioned at the cloning restriction site and in frame with the second promoter, whereby the second promoter mediates the transcriptional expression of the heterologous protein.

16. The baculovirus vector of claim 13 wherein the first or second promoter is the baculovirus immediate early gene IE1 or the baculovirus immediate early gene IEN.

* * * * *

UNITED STATES PATENT AND TRADEMARK OFFICE
CERTIFICATE OF CORRECTION

PATENT NO. : 5,162,222

DATED : November 10, 1992

INVENTOR(S) : Linda A. Guarino and Donald L. Jarvis

It is certified that error appears in the above-indentified patent and that said Letters Patent is hereby corrected as shown below:

On the Title page, please add: --[73] Assignee: The Texas A&M University System, Colege Station, Tex.--.

Column 1, line 64 delete "209" and replace with --2091--.

Column 3, line 28 delete "TM".

Column 4, line 65 delete "flankink" and replace with --flanking--.

Column 8, line 58 delete "ma" and replace with --may--.

Column 11, line 58 delete "BolI" and replace with --BglII--.

Column 12, line 28 delete "BolI" and replace with --BglII--.

Column 15, line 38 delete "IEIFB5" and replace with --IE1FB5--.

Column 17, line 15 add --.-- after "cells".

UNITED STATES PATENT AND TRADEMARK OFFICE
CERTIFICATE OF CORRECTION

PATENT NO. : 5,162,222

DATED : November 10, 1992

INVENTOR(S) : Linda A. Guarino and Donald L. Jarvis

It is certified that error appears in the above-indentified patent and that said Letters Patent is hereby corrected as shown below:

Column 23, line 4 delete "t" and replace with --to--.

Signed and Sealed this

Twenty-ninth Day of March, 1994

Attest:

BRUCE LEHMAN

Attesting Officer

Commissioner of Patents and Trademarks